ent, for example, a Mueller osteotomy saw, includes a coupling having a spindle which forms a mounting surface, the spindle being driven with the coupling by the power source. Located on the spindle is a locking pin assembly movable between a locking and an unlocking position, the spindle cooperating with a plurality of concentrically disposed latching pins which latch the medical instrument to the spindle in driving relationship therewith. The medical instrument, for example, a saw blade, includes a predetermined number of apertures corresponding to the number of latching pins on the spindle, each of the apertures including a pin receiving end and a latching end. Eccentrically positioned with respect to the apertures is a locking pin receiving aperture through which the locking pin on the spindle is received. The instrument is assembled over the locking pin which has been depressed, moved such that the latching pins are received by the latching pin apertures, and then manipulated such that the latching pins are urged into the latching end of the apertures. Upon release of the now aligned locking pin which includes an outer tapered surface, the mounted instrument is fixed and locked with respect to the spindle. To release the instrument, or to alter its position, the locking pin is depressed, the instrument moved such that the latching pins are aligned with the pin receiving portion of the apertures, and the instrument can either be rotated by relocating same to its desired position or replaced by another instrument.

United States Patent [19]

Bent

[11] 3,943,934
[45] Mar. 16, 1976

[54] QUICK RELEASE MECHANISM FOR SURGICAL DEVICES
[75] Inventor: John H. Bent, Carpinteria, Calif.
[73] Assignee: Minnesota Mining and Manufacturing Company, St. Paul, Minn.
[22] Filed: Sept. 30, 1974
[21] Appl. No.: 510,222

[52] U.S. Cl. .................... 128/317; 24/223; 30/339; 403/321
[51] Int. Cl.² ......................................... A61B 17/14
[58] Field of Search..... 24/203, 204, 205.18, 211 K, 24/223; 30/166, 337, 339; 128/317; 145/3 SE; 403/321, 322, 325, 349, 353

[56] References Cited
UNITED STATES PATENTS

| | | | |
|---|---|---|---|
| 726,732 | 4/1903 | Nelson | 403/321 |
| 2,422,693 | 6/1947 | McArthur | 24/223 |
| 2,557,364 | 6/1951 | Treace | 128/317 |
| 2,783,537 | 3/1957 | Gringer | 30/339 X |
| 3,554,197 | 1/1971 | Dobbie | 128/317 |

Primary Examiner—Channing L. Pace
Attorney, Agent, or Firm—Alexander, Sell, Steldt & DeLaHunt

[57] ABSTRACT
A quick release device for a powered surgical instru-

18 Claims, 6 Drawing Figures

U.S. Patent  March 16, 1976  3,943,934
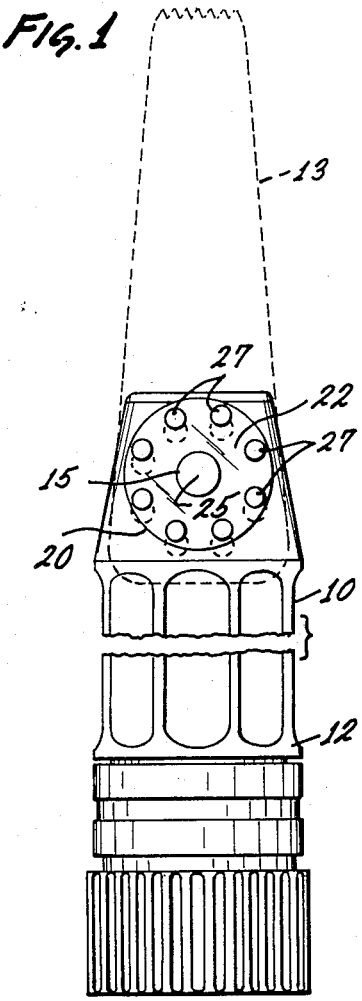
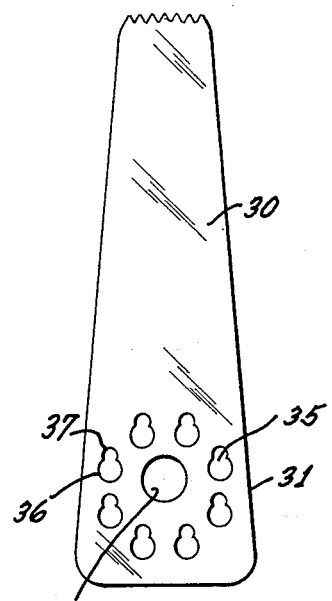
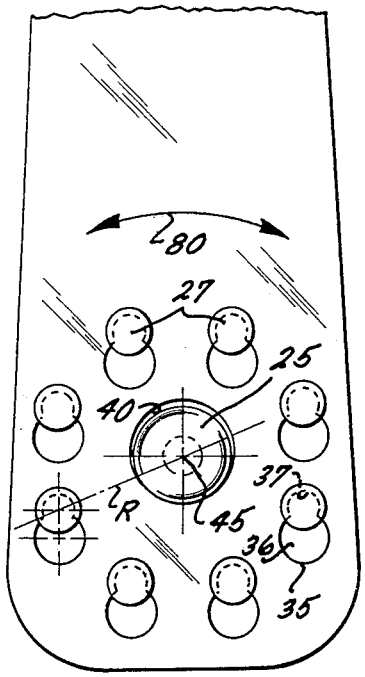
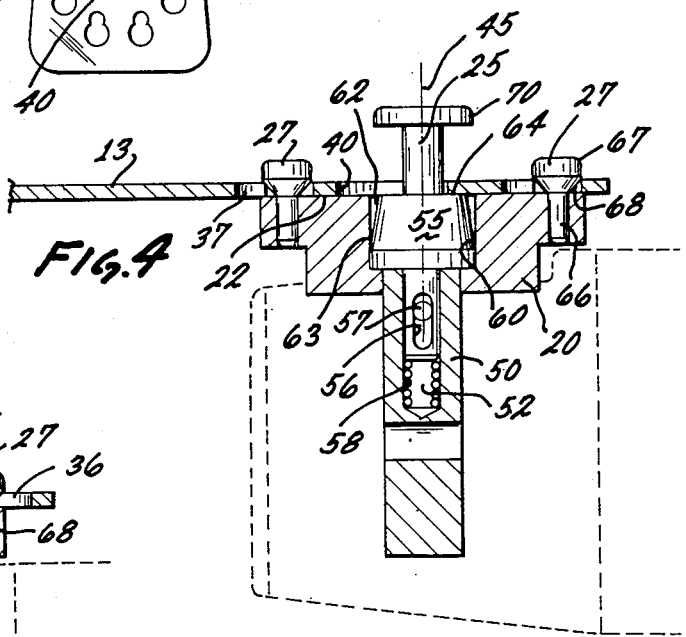
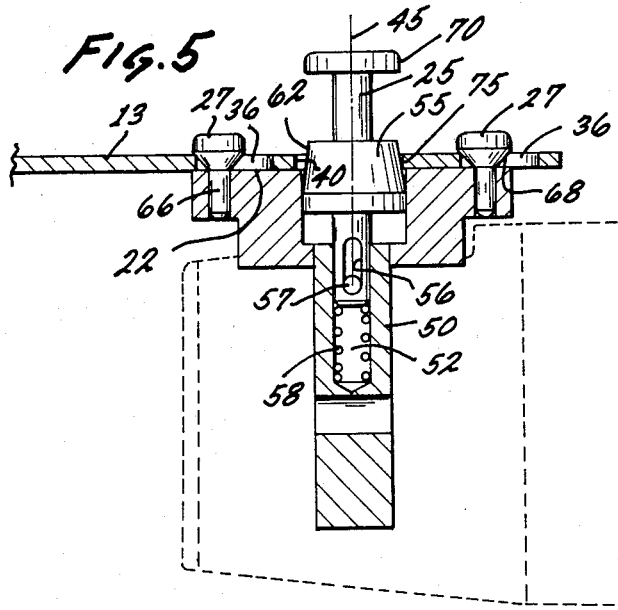
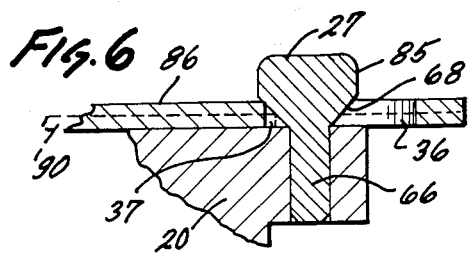

QUICK RELEASE MECHANISM FOR SURGICAL DEVICES

BACKGROUND OF THE INVENTION

The present invention relates to a medical instrument, and more particularly to a quick release mechanism for a medical instrument and an improved quick release mounting arrangement by which a medical instrument may be easily and effectively locked to a power source, and removed therefrom or which may be easily adjusted to a different orientation with respect to the power source.

Many surgical procedures are carried out with the use of a powered instrument, usually a driven rotary power device to which various auxiliary elements are attached to permit rotating, oscillating or reciprocating movement of the medical instrument.

In the case of osteological procedures, various medical instruments are used, such as an osteotomy saw, in which the configuration of the saw blade may vary from small to large, narrow to wide, a single or double bladed saw assembly.

Of the above types of devices, there is a device known in the art as a Mueller osteotomy saw used for femoral osteotomies in which angular depth control and line of sight observation are needed during the surgical procedure.

In the osteotomy saws of the prior art, change of blades, or orientation of the blades with respect to the power source for the purpose of maintaining a proper line of sight or angular depth control was accomplished by loosening a nut mounted over the saw blade, replacing the blade or changing its position and then retightening the nut. The blade normally includes a central aperture which is received over the spindle with a plurality of small apertures concentrically disposed with respect to the spindle receiving aperture. While devices of this type operate satisfactorily, there has been some criticism of such devices by the using surgeon because of the necessity to manipulate a locking nut to release the saw blade for the purpose of changing saw blades or changing its orientation.

Accordingly, it becomes apparent that a simple, efficient quick release mechanism which does not require any tools in order to change a blade or to alter its orientation is quite desirable. In such a system, it is important that the instrument mounted for powered movement be firmly secured to the power source, and easily removed and replaced, or easily changed in orientation with respect to the power source. Also, it is quite desirable to provide such a quick release mechanism which may be easily used with presently existing drive equipment.

SUMMARY OF THE INVENTION

The above desired objectives are achieved in accordance with the present invention by a quick release mechanism which is adapted to be mounted on an appropriate power source and powered thereby, wherein the quick release mechanism includes a medical instrument mounting portion which is received in driving relationship with the power source through a coupling. Cooperating with the coupling and forming a mounting surface which receives the medical instrument is a spindle assembly which includes a predetermined number of latching pins circularly arranged with respect to a center reference axis defined by a locking pin assembly movable from a locking position to an unlocking position. The locking pin assembly is spring urged to the locking position, and includes an outer tapered surface portion which cooperates with the medical instrument to be mounted on the quick release mechanism to assure locking engagement therewith.

The medical instrument itself includes a flat end to be received on the mounting surface of the spindle, the flat end of the instrument including a predetermined number of latching apertures, corresponding in number to the number of pins, each latching aperture including a pin receiving portion and a latching portion.

Cooperating with the apertures on the medical instrument itself is a locking pin assembly receiving aperture which is eccentrically positioned with respect to the latching pin receiving apertures, the medical instrument being received in latching relationship on the mounting surface of the spindle by engagement of the latching pins with the latching end of the apertures.

To assemble the medical instrument to the spindle, the locking pin assembly is depressed, the instrument aligned over the power source such that the latching pin apertures therein, and more specifically the pin receiving portions thereof are each aligned with one of the latching pins. The medical instrument is then placed flat against the mounting surface such that each of the latching pins projects through one of the corresponding apertures provided in the instrument. In this relative position, the locking aperture in the medical instrument is misaligned with respect to the locking pin assembly. As the medical instrument is moved to cause the latching pins to enter the latching portion of the locking apertures, the aperture in the instrument is aligned with the locking pin and release of the locking pin secures the instrument in place by virtue of the tapered surface which tends to urge the instrument in a direction which assures that the latching pins remain seated in the latching portion of the apertures.

To change the instrument, or to change its orientation with respect to the power source, the locking pin assembly is depressed, the instrument moved to a position where the latching pins are now aligned with the pin receiving portion of the apertures, the instrument is raised above the plurality of latching pins on the spindle to free the same from the spindle, either rotated to the desired position or removed from the locking pin assembly and replaced by another blade. The locking procedure is as already described.

One of the features of the present invention is the use of a plurality of latching pins which include a tapered portion such that medical instruments of different cross-sectional thickness may be received by the same spindle.

It will be apparent to those skilled in the art that the apparatus of the present invention is not to be considered to be limited by the specific constructions described herein. Rather, the specific construction described herein is illustrative of a preferred form of the present invention, and other embodiments and modifications will become apparent to those skilled in the art upon reading the following detailed description.

BRIEF DESCRIPTION OF THE DRAWINGS

FIG. 1 is a diagrammatic plan view of a power source including the quick release mechanism of the present invention and having mounted thereon a medical instrument in the form of an osteotomy saw constructed in accordance with the present invention;

FIG. 2 is a plan view of an osteotomy saw constructed in accordance with the present invention for use with the quick release mechanism of the present invention;

FIG. 3 is an enlarged plan view showing the relationship between the medical instrument in accordance with the present invention and the quick release mechanism as constructed in accordance with the present invention illustrating the geometry thereof;

FIG. 4 is a view partly in section and partly in elevation of the medical instrument and quick release mechanism of the present invention showing the unlocked position and the relationship of the parts;

FIG. 5 is a view similar to FIG. 4 but illustrating the locked position of the quick release mechanism and the medical instrument constructed in accordance with the present invention; and FIG. 6 is an enlarged fragmentary section showing the relationship between the latching pins and the medical instrument constructed in accordance with the present invention.

DETAILED DESCRIPTION OF THE INVENTION

Referring to the drawings which illustrate a preferred form of the invention, FIG. 1 shows a powered surgical device 10 known in the art as a Mueller osteotomy saw. In the form illustrated in FIG. 1, the saw includes an adapter 12 used to translate rotary motion into oscillating motion such that a saw blade 13 is caused to oscillate at a relatively high speed, for example 23,000 cycles per minute.

The internal workings of the adapter are well known, the adapter being in turn powered by a rotary power device such as a gas powered driver, or other suitable power device.

As previously mentioned, it is frequently necessary during the course of an osteointervention procedure to vary the position of the blade 13 with respect to the adapter 12, or, in the alternative, to use a blade of a configuration different from that illustrated in FIG. 1. Accordingly, the adapter 12, which may be considered the power source for the blade 13, is provided with a quick release mechanism generally indicated 15 which may be easily manipulated by the surgeon without the need of any tools in order to effect change of the position of the blade 13 relative to the power source, or to replace the blade 13 with another blade.

In general, the quick release mechanism 15 includes a coupling (FIG. 5) which is connected to the power source, the coupling including a mounting spindle 20 having a mounting surface 22, the spindle being driven with the coupling by the power source.

Cooperating with the spindle 20 is a locking pin assembly 25 movable between a locking position and an unlock position. Concentrically disposed with respect to the locking pin 25 are a plurality of latching pins 27, eight being shown for purposes of illustration. The latching pins are secured to the spindle 20 and move therewith. The latching pins 27 cooperate with the spindle and with the mounting surface 22 and the locking pin 25 to form a quick release locking device which may receive a medical instrument such as the osteotomy saw 13.

Referring to FIG. 2, a medical instrument 30 is illustrated in the form of an osteotomy saw, the saw having a mounting end 31 which includes a plurality of apertures 35 corresponding in number to the predetermined number of latching pins 27 provided on the spindle. Each of the apertures 35 includes a pin receiving end 36 which receives a latching pin 27, and a communicating latching end 37 which receives the associated latching pin in latching engagement. Eccentrically positioned within the apertures 35 which are circularly arranged is a locking pin receiving aperture 40 through which the locking pin 25 is received to hold the blade 30 in locking engagement with the latching pins 27 which are firmly seated within the latching ends 37 of the apertures 35.

Referring to FIG. 3, it can be seen that when assembled to the spindle on the adapter, and assuming the center point 45 of the locking pin 25 as the reference point, each latching end 37 of each aperture 35 of the saw is on the same radius R with respect to the center point 45. The diameter of the latching end of the apertures 37 is smaller than the diameter of the pin receiving end 36 of the apertures, the center of the pin receiving portion of the aperture being slightly offset, as shown in the drawings. The locking pin receiving aperture 40 is eccentrically positioned with respect to the center point 45 of the locking pin 25, the offset of the aperture 40 being in the same direction that the latching end 37 bears with respect to each of the apertures 35. Accordingly, with the pin receiving end 36 of the apertures aligned with the corresponding latching pin elements 27, the aperture 40 is misaligned with respect to the locking pin 25.

Referring to FIG. 4, the quick release mechanism includes a coupling 50 which is secured in driving relationship to the power source, such as that described. The spindle is provided with an interior bore 52, the coupling being fixed to the spindle 20 such that the spindle moves with the coupling. Locking pin 25 is received within the bore 52 and includes a locking member 55 which travels with the pin, the lower end of which is slotted to receive a securing pin 57 which fits through the wall of the coupling 50. The axial length of the locking pin 25 is such that the lower portion of the bore may receive a coiled spring 58 which forms a resilient means urging the locking pin 25 out of the bore until its travel is stopped by pin 57.

As illustrated in FIG. 4, the spindle 20 includes an enlarged cavity 60 to receive the locking member 55 which travels with the locking pin 25. In the form illustrated, the wall 62 of the locking member is tapered such that the locking member assumes a generally frusto-conical shape at its upper end, the lower end 63 of the locking member 55 being generally cylindrical to form a bearing surface to guide the travel of the locking member within the aperture 60. In the lowermost position of the locking pin, as illustrated in FIG. 4, the top 64 of the locking member is even with or slightly recessed below the surface 22 of the spindle 20.

Each of the latching pins 27 is disposed radially outwardly of the center 45 of the locking pin, the radial dimensions of each latching locking pin 27 from the center line of the pin 25 being the same. Each latching pin 27 includes a straight shank 66 and an upper head portion 67 with the portion between the head 67 and the straight shank being tapered outwardly as indicated at 68.

In the form of the invention shown, there are a predetermined number of latching pins, 8, corresponding with the predetermined number of apertures 35 in the saw blade, again 8. The diameter of the enlarged pin receiving portion 36 of the apertures 35 is such that the pin receiving portions may clear the enlarged head 67 of the latching pins 27. The latching end 37 of each aperture 35 in the saw blade is proportioned to receive the tapered section 68 of the latching pins 27, but is of a diameter smaller than the diameter of the enlarged portion 67 of each latching pin 27.

In the assembly of a blade to the quick release mechanism 10, the locking pin 25 is depressed against the spring 58 by manually pushing the locking pin downwardly as viewed in FIG. 4 until it assumes the relative position therein indicated. Thereafter, the saw blade 13 is assembled over the spindle by positioning the latching pin receiving portion 36 of each of the apertures 35 such that each is in alignment with a corresponding latching pin 27. As indicated in FIG. 4, the aperture 40 in the blade is slightly larger than the head portion 70 of locking pin 25, the pin being of reduced diameter between the head 70 and the locking member 55 in order to provide a clearance space since the saw blade must be moved somewhat to the left as viewed in FIG. 4 relative to the spindle in order to obtain alignment between the enlarged portion 36 of the apertures 35 and the corresponding latching pin members 27.

With the locking pin 25 fully depressed, the saw blade is manipulated over the latching pin elements 27 which pass through the enlarged portion 36 of each of the apertures 35 and bears against the surface 22 of the spindle. Thus positioned, the saw blade is moved to the right, as viewed in FIG. 4 in order for the tapered portion 68 of the latching pins to be slideably moved into the latching end 37 of the apertures 35. As the saw blade moves to the right, as referred to in FIG. 4, the aperture 40 almost becomes aligned with the locking member 55, still depressed by virtue of depression of the locking pin 25, and release of the locking pin 25 results in a spring biased upward movement of the locking pin and locking member 55 to lock the saw blade 13 within the latching end 37 of each of the apertures 35.

The locked position of the blade 13 is illustrated in FIG. 5 wherein like reference numerals have been used for corresponding parts. As illustrated in FIG. 5, with the locking pin 25 released, the locking member 55 extends above the surface 22 of the spindle and through and above the aperture 40 in the saw blade 13. The tapered surface 62 of the locking member bears against the wall portion 75 of the aperture 40 to urge the blade 13 to the right as viewed in FIG. 5, thereby assuring latching engagement between the tapered portion 68 of each latching pin 27 and the corresponding latching end 37 of each aperture 35 provided in the saw blade.

By a comparison of FIGS. 4 and 5 it can be seen that in the locked position, the saw blade is urged to the right as viewed in FIG. 5 such that the latching pin receiving end 36 of each aperture 35 is out of alignment with the corresponding latching pin 27. Therefore, the purpose of the eccentric arrangement of the aperture 40 with respect to the center line 45 of the locking pin is to assure that the tapered surface 62 of the locking member continues to engage the wall portion 75 of the aperture 40 to maintain the latching end of each aperture securely aligned with the tapered portion 68 of each latching pin.

To remove a saw blade, or to change its relative orientation with respect to the gripped portion of the power device, the locking pin 25 is depressed to a position as illustrated in FIG. 4 and the saw blade 13 is moved to the left, as viewed in FIG. 5, until it assumes the position illustrated in FIG. 4, the blade being raised such that the apertures 36 clear the latching pins 27, and the blade may be removed by lifting it over the locking pin since the aperture 40 of the blade can now be aligned with the head 70 of the locking pin 25. In the event that the orientation of the blade is desired to be changed, the attending physician need only rotate the blade through an arc 80 as illustrated in FIG. 3 until the apertures 35 are in alignment with the latching pins, and then continue the assembly of the blade to the quick release mechanism as already described. By providing 8 pins, it is possible to obtain an orientation of the blade 13 at 45° intervals in an entire 360° circle.

Referring to FIG. 6, the details of the latching pins 27 are illustrated, the upper end 85 of the pin being generally cylindrical and of larger diameter than the straight shank 66, the diameter of the portion 85 of the latching pins 27 being such that the pin receiving portion 36 of each aperture 35 of the saw blade may clear the same. By providing tapered surfaces 68 which flair outwardly and which are located between the straight shank 66 and the cylindrical end 85 of each pin, it is possible to accomodate saw blades of different cross-sectional thickness. As illustrated in FIG. 6 saw blade 86 is someewhat thicker than saw blade 90, the latter shown in dotted lines, and accordingly, the tapered surface operates to secure the blade in fixed driving relationship with the spindle by holding the same in tight engagement therewith along the flat spindle surface 22, rotation of the saw blade relative to the spindle being prevented by the latching pins 27 which are firmly seated within the latching end 37 of each aperture 35.

While the above description, for the purposes of illustration, has made reference to a Mueller osteotomy saw in which the saw blade is moved in an oscillating manner, it will become apparent to those having skill in the art that the present invention may be used with saw blades of any of the shapes currently used in osteological procedures, as already described, and the power source may be one which provides rotary or reciprocating motion of the saw blade.

It will also be apparent, from the foregoing description, that the ease with which the position of the blade may be changed, or blades may be replaced by the quick release mechanism of the present invention satisfies the desires of the surgeon for a relatively simple, noncomplicated quick release mechanism which assures properly driving relationship between the driven medical instrument and the power source.

As previously mentioned, the quick release mechanism of the present invention has been designed such that it is interchangeable with the Mueller osteotomy attachment used to bring about oscillating motion of the saw blade. Moreover, the present design offers the advantage of accommodating blades of different cross-sectional dimensions because of the design of the latching pins, an added and significant feature of the present invention.

While the above description and accompanying drawings illustrate an exemplary embodiment of the preferred form of this invention, it will be understood by those skilled in the art that changes and modifications may be made to the various forms illustrated and described without departing from the scope of the invention as set forth in the apended claims.

I claim:

1. A medical instrument adapted to be moved by a power source and intended for quick release therefrom comprising a mounting portion for retention in driving relation with a power source,
said mounting portion including a predetermined number of apertures generally radially disposed with respect to a predetermined reference center point,
each aperture including a pin receiving portion and a latching portion, and
a locking pin aperture eccentrically located with respect to said predetermined reference center point whereby upon mounting of said instrument on the power source by alignment of the pin receiving portion of each of said predetermined apertures with its respective latching pin and displacing same to engage said latching pins with the latching portion of said apertures, said latching portions of said apertures are radially disposed with respect to said reference center point and said locking pin aperture is eccentric with said reference center point to permit wedging engagement thereof by a locking pin.

2. A medical instrument as set forth in claim 1 wherein said instrument is a saw.

3. A medical instrument as set forth in claim 2 wherein said saw is an oscillating osteotomy saw.

4. A medical instrument as set forth in claim 2 wherein said latching portion of said apertures are each equally positioned radially outwardly of said reference center point.

5. A medical instrument as set forth in claim 3 wherein said osteotomy saw includes an elongated body member with saw teeth at the portion thereof opposite said mounting portion.

6. A medical instrument as set forth in claim 5 wherein said latching portion of said apertures are each equally positioned radially outwardly of said reference center point.

7. A quick release mechanism for attaching a medical instrument to a source of power for powered movement of the instrument comprising:
coupling means for providing a driving connection to a power source,
means cooperating with said coupling means to form a mounting surface which receives said medical instrument for movement with said coupling means,
locking pin means cooperating with said mounting surface and movable between a locking position and an unlock position,
a predetermined number of latching pins radially disposed about said locking pin means with respect to the center axis thereof and projecting from said mounting surface, and
said locking pin means including a tapered surface portion extending above said mounting surface in the locking position of said locking pin means and operative to bear against a portion of said medical instrument mounted on said mounting surface to maintain the latter locked to said mounting surface by engagement of said latching pins with corresponding slots provided in said medical instrument.

8. A quick release mechanism as set forth in claim 7 wherein said locking pin means is biased to the locking position.

9. A quick release mechanism as set forth in claim 7 wherein said locking pin means includes a tapered surface a portion of which engages a medical instrument mounted over said latching pins and on said mounting surface to secure the same in driven relation with said quick release mechanism.

10. A quick release mechanism as set forth in claim 7 wherein each latching pin includes a head portion projecting above said mounting surface and an inwardly tapered shank positioned between said head portion and said mounting surface.

11. A quick release mechanism as set forth in claim 9 wherein said locking pin means includes a shank of reduced cross-section between the face end thereof and said tapered surface portion.

12. A quick release mechanism for attaching a movable medical instrument to a source of power for powered movement of said instrument comprising:
coupling means for providing a driving connection to a power source,
means cooperating with said coupling means to form a mounting surface which receives said medical instrument for movement with said coupling means,
locking pin means cooperating with said mounting surface and being movable from a locking position to an unlock position,
a plurality of latching pins on said mounting surface for receiving a medical instrument to be driven by the power source,
a medical instrument for mounting on said mounting surface and including means forming a plurality of apertures at least equal in number to said plurality of latching pins,
each said aperture including a pin receiving end which receives a latching pin and a communicating latching end which receives the associated latching pin in latched engagement,
said medical instrument including means defining a locking pin receiving aperture so arranged that as said locking pin means is moved to the unlock position, said medical instrument positioned with the plurality of apertures disposed such that said latching pin receiving ends are aligned with said latching pins to place said instrument in contact with said mounting surface and moved therealong to effect engagement between the latching end of said aperture and the corresponding latching pin whereby upon movement of said locking pin means to the locking position said medical instrument is held by said latching pins.

13. A quick release mechanism as set forth in claim 12 wherein said medical instrument is an osteotomy saw.

14. A quick release mechanism as set forth in claim 12 wherein said plurality of latching pins are so disposed as to provide for changing the position of said medical instrument at 45° intervals with respect to said locking pin means.

15. A quick release mechanism as set forth in claim 12 wherein the locking pin receiving aperture in said medical instrument is eccentrically positioned with respect to the apertures therein.

16. A quick release mechanism as set forth in claim 15 wherein said locking pin means forms a center reference point for said latching pins which are equally spaced radially from said locking pin means whereby said latching pin receiving ends of said apertures are eccentrically oriented with respect to said center reference point while said latching end of said apertures are equally spaced radially of said locking pin means with said medical instrument locked to said mounting surface.

17. A quick release mechanism as set forth in claim 12 wherein each of said latching pins includes a head portion projecting above said mounting surface and an inwardly tapered shank positioned between said head portion and said mounting surface.

18. A quick release mechanism as set forth in claim 12 wherein said locking pin means includes a tapered surface a portion of which engages a medical instrument mounted over said latching pins and on said mounting surface to secure the same in driven relation with said quick release mechanism.

* * * * *